(12) United States Patent
Makeeva et al.

(10) Patent No.: US 12,205,713 B2
(45) Date of Patent: Jan. 21, 2025

(54) SYSTEMS AND METHODS FOR AUTOMATICALLY IDENTIFYING AND TRACKING MEDICAL FOLLOW-UPS

(71) Applicants: Emory University, Atlanta, GA (US); Children's Healthcare of Atlanta, Inc., Atlanta, GA (US)

(72) Inventors: Valeria Makeeva, Atlanta, GA (US); Peter Harri, Atlanta, GA (US); Nabile Safdar, Atlanta, GA (US); Kyle Jackson, Atlanta, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 88 days.

(21) Appl. No.: 17/573,390

(22) Filed: Jan. 11, 2022

(65) Prior Publication Data

US 2022/0223271 A1 Jul. 14, 2022

Related U.S. Application Data

(60) Provisional application No. 63/135,790, filed on Jan. 11, 2021.

(51) Int. Cl.
*G06Q 50/22* (2024.01)
*G06Q 10/10* (2023.01)
(Continued)

(52) U.S. Cl.
CPC ............. *G16H 40/20* (2018.01); *G16H 10/60* (2018.01); *G16H 50/20* (2018.01)

(58) Field of Classification Search
CPC ........ G16H 40/20; G16H 10/60; G16H 50/20; G16H 50/70; G16H 80/00
See application file for complete search history.

(56) References Cited

U.S. PATENT DOCUMENTS

2014/0278448 A1* 9/2014 Sadeghi ................ G06Q 10/10
705/2
2015/0193583 A1 7/2015 McNair et al.
(Continued)

OTHER PUBLICATIONS

Dibble et al. The RADCAT-3 system for closing the loop on important non-urgent radiology findings: a multidisciplinary system-wide approach. Emergency Radiology. 2017; 24(2):119-125.
(Continued)

*Primary Examiner* — Maroun P Kanaan
(74) *Attorney, Agent, or Firm* — Emory Patent Group

(57) ABSTRACT

The systems and methods of the disclosure can rapidly and automatically determine and monitor tracking events by generating event codes using messages from multiple source systems within the healthcare ecosystem. The method may include detecting one or more healthcare data messages of a plurality of types of healthcare data messages associated with healthcare of a patient. The method may include extracting text of each message of the first type and processing the extracted text of each message to determine one or more units of text. The method may include determining one or more tracking events by applying one or more trained models to each unit of text of each message. The method may include storing one or more event codes corresponding to the one or more tracking events and its associated deadline in a record for the patient of the tracking event database.

20 Claims, 5 Drawing Sheets

(51) Int. Cl.
  *G16H 10/60* (2018.01)
  *G16H 40/20* (2018.01)
  *G16H 50/20* (2018.01)

(56) References Cited

U.S. PATENT DOCUMENTS

| | | |
|---|---|---|
| 2020/0105391 A1 | 4/2020 | Komirishetty et al. |
| 2020/0117860 A1 | 4/2020 | Anand et al. |
| 2020/0118660 A1 | 4/2020 | Sevenster et al. |
| 2020/0161003 A1 | 5/2020 | Wright et al. |
| 2020/0321100 A1 | 10/2020 | Glottmann et al. |
| 2020/0342967 A1 | 10/2020 | Bronkalla et al. |
| 2020/0381092 A1 | 12/2020 | Granvold et al. |
| 2021/0029535 A1 | 1/2021 | Stuber et al. |
| 2021/0201240 A1 | 7/2021 | Yanamala et al. |
| 2021/0365849 A1 | 11/2021 | Kamen et al. |

OTHER PUBLICATIONS

Dutta et al. Automated detection using natural language processing of radiologists recommendations for additional imaging of incidental findings. Annals of Emergency Medicine. 2013; 62(2):162-169.
William G. Geiger. Automated Flagging and Tracking for Incidental and Modified Radiology Reports for ED Patients. SIIM 2019 Annual Meeting. Jun. 26, 2019-Jun. 28, 2019; Denver, Colorado.

\* cited by examiner

SYSTEMS AND METHODS FOR AUTOMATICALLY IDENTIFYING AND TRACKING MEDICAL FOLLOW-UPS

CROSS-REFERENCE TO RELATED APPLICATIONS

This application claims the benefit of U.S. Provisional Application No. 63/135,790 filed Jan. 11, 2021. The entirety of this application is hereby incorporated by reference for all purposes.

BACKGROUND

Incidental findings have been reported in 10 to 30% of imaging studies with 5% of reports recommending further workup. These findings can present an opportunity to address a serious medical condition at an early treatable stage and reduce morbidity. However, an estimated 10-60% of patients fail to receive the recommended workup. This failure represents a patient safety threat and relates to the Center for Medicare and Medicaid Services (CMS) Meaningful Measures framework within the Quality Payment Program (QPP) and Hospital Value-Based Purchasing (HVBP) Program.

Current efforts tracking incidental findings have relied on semi-automated processes that are not performed in real-time. These semi-automated efforts also have not been widely disseminated and have failed to scale to the necessary report volume.

SUMMARY

Thus, there is a need for efficient and automatic determination of tracking events based on incidental findings in real-time and monitoring thereof.

In some embodiments, the methods may include a computer-implemented method for determining and/or monitoring a tracking event. In some embodiments, the method may include detecting one or more healthcare data messages of a plurality of types of healthcare data messages associated with healthcare of a patient. The plurality of types of healthcare data messages may include a first type and one or more of other types of healthcare data messages. The method may further include extracting text of each message of the first type. The method may further include processing the extracted text of each message to determine one or more units of text. The method may also include determining one or more tracking events by applying one or more trained models to each unit of text of each message. The method may include storing one or more event codes corresponding to the one or more tracking events in a record for the patient in a tracking event database. The one or more event codes may be associated with a deadline for satisfaction.

In some embodiments, the systems may include a determining and/or monitoring a tracking event. The system a memory and one or more processors. In some embodiments, the one or more processors may be configured to cause detecting one or more healthcare data messages of a plurality of types of healthcare data messages associated with healthcare of a patient. The plurality of types of healthcare data messages may include a first type and one or more of other types of healthcare data messages. The one or more processors may be configured to cause extracting text of each message of the first type. In some embodiments, the one or more processors may be configured to cause processing the extracted text of each message to determine one or more units of text. In some embodiments, the one or more processors may be further configured to cause determining one or more tracking events by applying one or more trained models to each unit of text of each message. In some embodiments, the one or more processors may be configured to cause storing one or more event codes corresponding to the one or more tracking events in a record for the patient in a tracking event database. The one or more event codes may be associated with a deadline for satisfaction.

In some embodiments, the systems may include a system for determining and/or monitoring a tracking event. The system may include one or more databases. The one or more databases may include a tracking event database for storing tracking event information. The system may include a detection module that includes a plurality of listeners configured to detecting one or more messages of a plurality of types of healthcare data messages. The plurality of types of messages may include a first type and one or more of other types of healthcare data messages. Each listener may be configured to detect a specific type of healthcare data message. In some embodiments, the system may include a text processing module configured to process the first type of healthcare data message into one or more units of text. In some embodiments, the system may include a tracking determination module configured to determine one or more tracking events based on the one or more units of text by applying one or more of trained models to each unit of text. In some embodiments, one or more tracking event codes may correspond to the one or more tracking events being stored in a record for the patient in the tracking event database. In some embodiments, the system may further include a monitoring module configured to monitor a tracking event stored in the tracking event database using the plurality of types of healthcare data messages according to the corresponding monitoring pattern associated with the event code.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, the emphasis being placed upon illustrating the principles of the disclosure.

DESCRIPTION OF THE EMBODIMENTS

Figure 1:
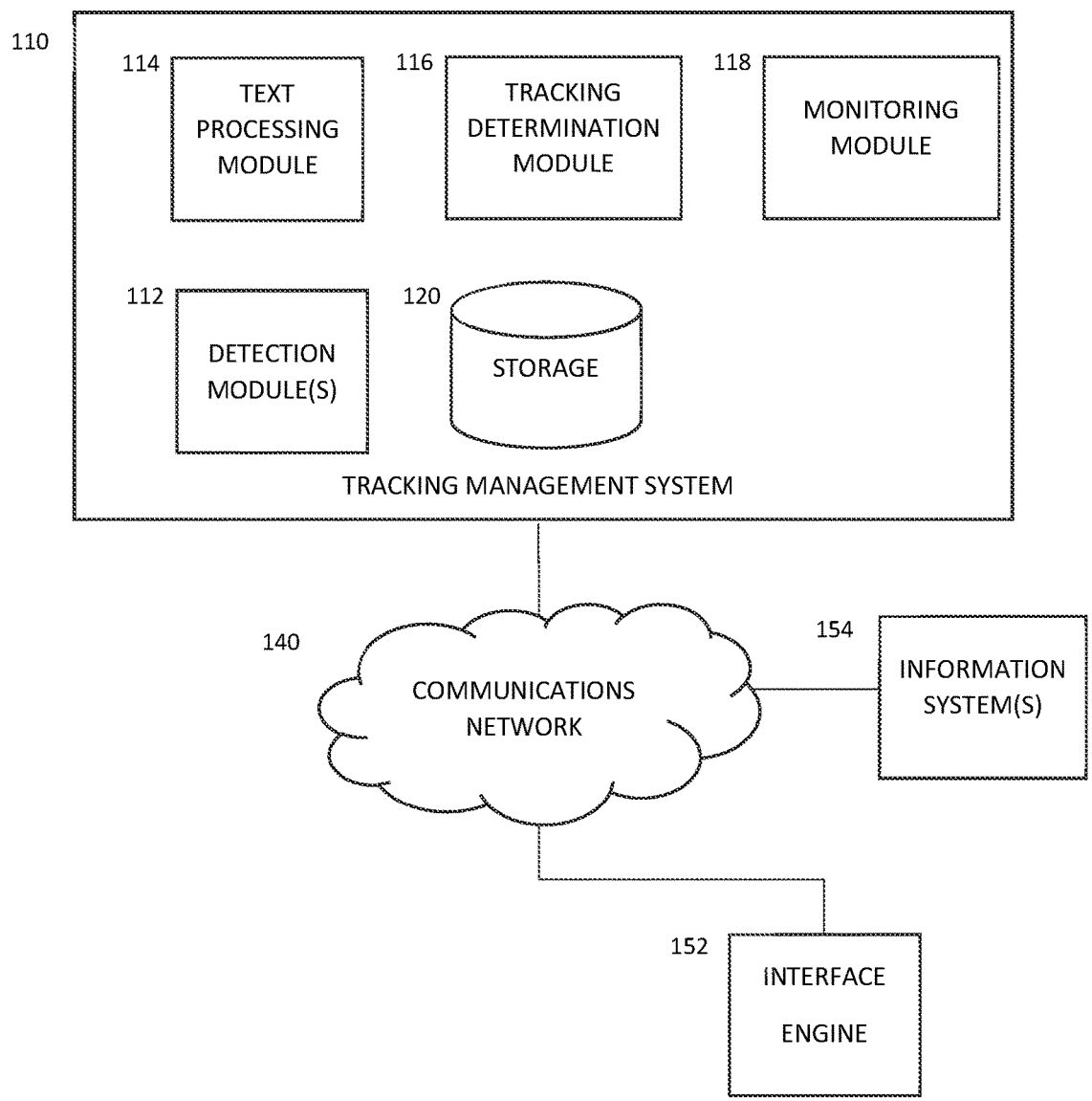
FIG. 1 illustrates an example of system environment for generating and monitoring tracking events using healthcare messages according to embodiments.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The disclosed embodiments relate to techniques for automatic, efficient, and accurate identification and monitoring of a tracking event (recommendation). A tracking event (also referred to as a "follow-up" event) may relate to an incidental finding recommendation. The embodiments can identify a tracking event basically in real-time and monitor that follow-up event from the exchange of data message(s) between source and target systems in a healthcare ecosystem. For example, the one or more data messages (also referred to as "messages") may include but are not limited to a healthcare message associated with one or more aspects of a clinical record, opening a record(s) for new patient(s), receiving a transferred patient, reviewing and reporting on an image, and/or any other instance and/or situation that requires or dictates responsive action or processing, among others, or a combination thereof. The healthcare message may be according to (health level seven) HL7 standard format. For example, the one or more messages may include but are not limited to Patient Administration Messages (HL7 admit discharge transfer (ADT)), Orders (HL7 order entry message (ORM)), Charges (HL7 DFT), Results (HL7 observation result (ORU)), Schedule information (HL7 scheduling information unsolicited (SIU)), Referral (HL7 REF), Image order, Pharmacy order, Clinical Documents (CDA), among others, or any combination thereof.

The disclosed embodiments can combine information from one or more messages from multiple source systems within the healthcare ecosystem across different timeframes (e.g., hours, days, months, etc.) to generate a tracking event. By way of example, the disclosed embodiments can use multiple listeners that can be specific to the message type that can work in tandem to generate a unique tracking event as well as monitor the tracking event, across the multiple applications associated within a healthcare ecosystem. By generating and storing the unique tracking event, the disclosed embodiments can more quickly process these messages, so that the messages can be processed in substantially real-time. The disclosed embodiments can therefore handle a high data volume, as well as being vendor neutral.

The disclosed embodiments provide a common language through which disparate systems and multiple languages over different timeframes within a healthcare ecosystem can communicate and be understood to automatically determine and monitor a follow-up recommendation using a "new" tracking event generated using the disclosed embodiments. By way of example, the disclosed embodiments determines a "new" event code that defines a tracking event and associated monitoring rules (e.g., monitoring pattern (activation (e.g., monitoring) pattern, a deadline, among others, or a combination thereof) using information across the multiple disparate systems. In some examples, by using the event code and the disclosed system architecture (e.g., a combination of HL7 listeners, deep neural nets, and database storage associated with event codes), the disclosed embodiments can enable a framework in which these systems can communicate using the same "language" across multiple systems and timeframes. The disclosed embodiments thereby allow information that was previously unable to be obtained, due to the different languages of the disparate systems and the different (often months) timeframes of information, to now be understandable and clinically actionable. For example, if the tracking event is not satisfied, the system can automatically transmit a notification requiring clinical action by the provider to address the tracking event (e.g., a user interface enabling order to be placed, for example, within the specific patient chart, a user interface enabling one or more reason for not satisfying the tracing event to be selected, etc.) thereby closing the clinical loop. Thus, the disclosed embodiments can efficiently automate the follow-up process and the clinical loop, thereby resulting in improved healthcare outcomes.

It will be understood that the disclosure is not limited to the messages and HL7 standard discussed herein and may include other messages and standards. For example, the support healthcare standard protocols may include but is not limited to Clinical Document Architecture (CDA), Integrating the Healthcare Enterprise's (IHE's) Cross-Enterprise Document Sharing (XDS), Patient Identity Cross-Referencing/Patient Demographics Query (PIX/PDQ), Audit Trail and Node Authentication (ATNA), HL7 Fast Healthcare Interoperability Resources (FHIR), other IHE profiles, or any combination thereof.

Various embodiments are described herein, including systems, methods, devices, modules, models, algorithms, networks, structures, processes, computer-program products, and the like.

FIG. 1 depicts an example of a healthcare system environment 100 for determining and/or monitoring one or more tracking events according to embodiments. In some embodiments, the healthcare system environment 100 may include a tracking management system 110 configured to determine one or more tracking or follow-up events, such as an incidental finding recommendation that communicates with its healthcare information systems 154 via an interface engine. The healthcare information systems 154 may include but are not limited hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR), among others, or any combination thereof. Information stored/transmitted can include, for example, patient medication orders, medical histories, imaging data, test results, diagnosis information, management information, and/or scheduling information, among others, or a combination thereof.

In some embodiments, the management system 110 can combine healthcare data messages (also referred to as "messages") from the healthcare systems 154 (e.g., source applications) through one or more interface engines 152. This can result in a faster and more sophisticated analysis capable of handling high data volume and a system that is vendor-neutral. For example, the management system 110 may include one or more detection modules 112 that is configured to communicate directly with the interface engine(s) 152 to listen for incoming and/or outgoing messages from the systems/applications 154. For example, the detection module(s) 112 may include a plurality of listeners configured to listen for specific messages. For example, each listener may be configured to listen to a specific type of message, to a message associated with a specific patient record, among others, or a combination thereof. By way of example, the detection module(s) 112 may include a (first) listener (also referred to as "ORU" listener or "Results Message" listener) configured to listen for and acquire all result messages, such as an ORU message, received by an interface engine 152, a (second) listener configured to parse text from one or more sections and/or subsections, such as report text, of an acquired ORU message, among others, or a combination thereof. The detection module(s) 112 may additionally and/or alternatively include one or more other listeners configured to listen to other type of messages that are associated with a specific patient record, for example, stored in a tracking database (120). For example, the one or more other listeners may include a listener configured to listen to ORM messages, a listener configured to listen to ADT messages, a listener configured to listen to SIU messages, among others, or any combination thereof.

For example, for the ORU messages acquired by the ORU listener, the tracking management system 110 may determine the one or more tracking events (e.g., incidental finding recommendations) to be monitored by the system 110 (via the monitoring module 118) and/or monitor the one or more tracking events using the text from one or more sections of each ORU message. For example, the one or more tracking events may relate to clinic visits, procedures, other orders, and/or findings requiring additional clinical information. By way of example, the one or more tracking events may include but are not limited to two or more categories. The one or more categories may include a first category (no follow-up), a second category (incidental requiring a follow-up/tracking), among others, or a combination thereof. For the first category (i.e., no tracking or follow-up needed), the system 110 may determine that no event code needs to be generated and/or stored with regards to at least that section (s)/sub-section(s) of the message. By way of example, the second category (incidental requiring follow-up/tracking) may include an imaging follow-up, a procedure follow-up, a clinic visit follow-up, among others, or a combination thereof. For the second category, the system 110 may determine an event code, from a plurality of stored event codes, that corresponds to the specific tracking event (an imaging follow-up, a procedure follow-up, a clinic visit follow-up, among others, or a combination thereof).

In some examples, the one or more tracking events may also be determined using additional information of the patient, such as demographic status, health status, tobacco use (e.g., smoking) status, among others, or any combination thereof. By way of example, the imaging follow-up may relate to a nodule with imaging follow-up determined by smoking status.

In some embodiments, the tracking management system 110 may store each ORU message received by the ORU listener in one or more databases (storage 120) while the tracking management system 110 processes that message to determine one or more tracking events and/or to determine whether a tracking event is satisfied. For example, the storage 120 may include one or more databases. By way of an example, the storage 120 may include a tracking database (also referred to as "follow-up database") configured to store the tracking event information (e.g., tracking event and associated records) to be monitored and/or processed for each patient (e.g., for example, by being stored with an associated patient identifier). In some embodiments, the tracking database may be configured to store the patient information that have one or more tracking events identified and monitored by the tracking management system 110 with the associated patient identifier. In some examples, the patient identifier may correspond to the patient identifier included in the received message, the EMR, among others, or any combination thereof. For example, the patient identifier may correspond to the Enterprise Master Patient Index (EMPI) number.

In some embodiments, the tracking database may also be configured to store the patient information while the ORU message is being processed. In other embodiments, the system 110 may include one or more additional databases configured to store the patient information and/or ORU message information before and/or while the ORU message is being processed to determine/identify one or more tracking events. In some embodiments, the one or more additional databases may include one or more routing databases in which the ORU message may be stored in a queue for processing. In some embodiments, the storage 120 may also include an analysis database configured to store information for each ORU message processed, including those determined to have no tracking event, tracking event identified and satisfied, among others, or a combination thereof.

For example, the analysis database may store at least the patient information included in the tracking database. In some embodiments, the analysis database may also store additional information regarding the follow-up/tracking event. The additional information may include but is not limited to follow-up exam information (for imaging or procedures) (e.g., type including body region and modality; order placed date and time, exam completed date and time; ordering provider; etc.), return office visit information (type including primary care physician (PCP), Emergency Room (ER), sub-specialty, etc.; visit completed date and time; provider; etc.) among others, or a combination thereof.

The information stored in the tracking database may be determined using at least the ORU message. By way of example, the patient information stored in the tracking database may include but is not limited to demographics (e.g., patient age, medical record number (MRN), patient gender, patient name, zip code, insurance info, smoking status, patient identification, etc.), initial exam information (e.g., type, date and time, ordering provider, etc.), among others, or a combination thereof. The tracking database may also store the tracking event for each patient record.

In some embodiments, the system 110 may include a tracking determination module 116 configured to determine one or more tracking events using the ORU message. In some embodiments, the system 110 may include a text processing module 114 configured to process the ORU message before the tracking determination module 116.

In some embodiments, the text processing module 114 may be configured to process one or more sections of the ORU message into units of text. The units of text may be in a form of a matrix. For example, the units of text may be a count-based matrix (e.g., number of times certain words or phrases i.e., tokens occur). In some embodiments, the text processing module 114 may include a plurality of tokenizers. For example, the plurality of tokenizers may be configured to tokenize every word in one or more sections, one or more subsections of the one or more sections, among others, or any combination thereof, of the ORU message. By way of example, the plurality of tokenizers may be configured to tokenize the text in one or more subsections of the Report Section, such as Impression Subsection (e.g., a radiology report impression), Technique Subsection, Finding Subsection, Organ-By Organ Subsection, Report Title, Clinical Indication Subsection, Comparison To Priors Subsection, etc. of the ORU message into a matrix. In other examples, the plurality of tokenizers may be configured to tokenize the text in additional and/or alternative sections, such as organ-by-organ description, report subsections, among others, among others, or any combination thereof.

In some embodiments, the tracking determination module 116 may be configured to determine one or more tracking events using the one or more units of text. In some embodiments, the tracking determination module 116 may determine/identify one or more tracking events by using one or more trained models developed using machine learning, for example, stored in the storage 120.

In some embodiments, the system 110 may include a plurality of trained models specific to one or more tracking variables, tokenized text from one or more sections and/or subsections of messages, among others, any combination thereof. For example, the one or more tracking variables may include but are not limited to type and/or characteristics of finding (e.g., thyroid nodules, aortic aneurysms, pneumonia, pulmonary nodules, adrenal nodules, etc.; its dimensions (e.g., mm), location appearance, etc.; among others, or any combination thereof), type of procedure, type of clinic visit, among others, or any combination thereof. By way of example, each trained model may be trained using one or more different tracking variables and tokenized text. In some examples, the trained models may be stored in the storage 120.

In some embodiments, each trained model may be a deep neural network. By way of example, the deep network may be a 8-layered structure. For example, each model may be trained by learning words from the radiology reports that have been process by using a natural-language processor and tokenized to create its own filters (e.g., feature maps) and memorizing the patterns that have the highest frequency. In some examples, the one or more models may have dropout layers that reduce the number of parameters and reduces over-fitting and long-short term memory (LSTM) layers that have memory nodules to remember previous patterns in the report. During training, each model (network) may run multiple epochs in which the output is compared to the ground truth (i.e. the labeled reports) then reweigh the inputs multiple times until achieving the best performance.

In some embodiments, the one or more trained models may be a long short term neural (LSTN) network which performs well with text classification tasks. See FIG. 3 for an example of training a model specific to one or more training variables. In other embodiments, one or more models may include additional and/or alternative neural and/or non-neural networks. For example, the one or more models may be a random-forest model.

In some embodiments, each (second category) tracking event may be identified by an event code in the database. Each (second category) tracking event may have monitoring rules specific to that event code. In some examples, the monitoring rules may include an activation (e.g., monitoring) pattern, a deadline, among others, or a combination thereof. The activation pattern may include one or more actions defined by one or more messages (e.g., SIU, ADT, ORM, ORU) that satisfy the tracking event in a record, monitoring interval, among others or a combination thereof. For example, the one or more actions (e.g., message(s)) may depend on the type of event (e.g., clinic visit type, findings requiring clinical information, etc.). In some embodiments, each tracking event code may have a specific monitoring interval (e.g., 2 weeks from the deadline). In some embodiments, a plurality of event codes, including its associated monitoring rules (e.g., the activation pattern, deadline, etc. for each event code), may be stored in the storage 120 and predefined by the system 110.

In some embodiments, the system 110, using the monitoring module 118, may cause the detection module 112 (e.g., HL7 listeners) to query the tracking database according to the different activation patterns at a predefined monitoring interval (e.g., 2 weeks or other defined period past the defined period (i.e., deadline) associated with the event code), for example, to determine an alert action (e.g., notification). In some examples, the alert action may be a clinically actionable communication that enables one or more clinic actions, such as ordering a procedure, identify reason(s) for failure to satisfy the tracking event by the deadline indicated by the event code, among others, or a combination thereof. For example, the communication may include a user interface that allows one-click ordering with EMR, a user interface (e.g., checkbox) that allows selection of one or more reasons for failure to satisfy the tracking event by the deadline indicated by the event code, among others, or a combination thereof. For example, the one or more reasons to be displayed for selection may include but is not limited to (i) follow-up imaging was obtained elsewhere, (ii) patient is deceased, (iii) follow-up is not felt to be clinically necessary for a specific reason, (iv) follow-up is not felt to be clinically necessary with a blank field for the reason to be completed by the provider, (v) among others, or (vi) any combination thereof.

By way of example, if the stored event code corresponds to a clinic visit type for a patient record (i.e., associated with a patient identifier) in the tracking event database, the system 110 may check for new SIU and ADT at the interval for that patient corresponding to that patient identifier. If a new SIU is not created by the deadline indicated by the event code (e.g., 2 weeks or other defined period past the defined period (i.e., deadline) associated with the event code) for that patient, the system 110 may cause an alert action, such as a clinically actionable communication to be sent to the provider with regards to that patient.

By way of another example, if the stored event code corresponds to a procedure-type for a record, the system may check for new SIU, ORM, ADT, and ORU messages. If no new ORM is created by the corresponding defined period (e.g., 2 weeks or other defined period past the defined period (i.e., deadline) associated with the event code) past the deadline, the system 110 may cause an alert action (e.g., clinically actionable communication) to be sent.

By way of another example, if the stored event code corresponds to a finding requiring clinical information for follow-up determination (pulmonary nodules) type, the system 110 may check for clinical information from EMR (smoking status). If the patient is high-risk (smoker), the system 110 may check for new ORM and/or new ORU messages. If no new ORM is created by the corresponding defined period (e.g., 2 weeks or other defined period past the defined period (i.e., deadline) associated with the event code) past the deadline, the system 110 may cause an alert action (e.g., clinically actionable communication) to be sent.

By way of another example, if the stored event code corresponds to an imaging (pneumonia, included for completeness) type, the system 110 may check for new ORM and new ORU. If no new ORM is created by the corresponding defined period (e.g., 2 weeks or other defined period past the defined period (i.e., deadline) associated with the event code) past the deadline, the system 110 may cause an alert action (e.g., clinically actionable communication) to be sent. It will be understood that the monitoring patterns are not limited to these examples and may include additional and/or alternative patterns for these types as well as additional types.

In some embodiments, the notification may include outputting a notification to the provider, entering a new diagnosis (e.g., "Outstanding Follow-up") into the patient chart, among others, or a combination thereof. In some examples, the alert action may be sent via the EMR so that the provider may order the procedure or clinic visit needed to satisfy the tracking event. In some examples, the alert action may include a user interface to enable a clinical action, such as one-click ordering (to enable an order to be placed, for example, within the specific patient chart), reason(s) for failure to satisfy the tracking event by the deadline indicated by the event code, among others, or a combination thereof.

In some embodiments, the module 112 may identify messages that satisfy the tracking event determined by the module 116 and stored in the tracking database (120). By way of example, the ORU listener may process ORU messages that include the patient information (e.g., patient identifier) corresponding to a record stored in the tracking database to determine whether the corresponding tracking event for that record has been satisfied, for example, using the text of the message having the same patient identifier. By way of example, the other listeners may be configured to identify SIU, ADT, and/or ORM messages that include the patient information corresponding to a record stored in the tracking database, for example, using the patient identifier. If the system determines that the tracking event is satisfied/completed for that patient, for example, using the text of the message having the same patient identifier, the system 110 may update the databases, for example, by moving that record from the tracking database to the analysis database. In some embodiments, the system 110 may remove that tracking event from the tracking database without adding that record to the analysis database.

In some embodiments, the system 110 may include any computing or data processing device consistent with the disclosed embodiments. The system 110 may transmit and receive data across a communications network (e.g., the network 140).

By way of example, the communication network 140 can include one or more networks such as a data network, a wireless network, a telephony network, or any combination thereof. The data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, NFC/RFID, RF memory tags, touch-distance radios, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof. The system 110 may further implement aspects of the disclosed embodiments without accessing other devices or networks, such as network 140.

The system 110 may include one or more computing systems for processing, storing, receiving, obtaining, and/or transmitting information, such as computing system 500 described in connection with FIG. 5. In some aspects, the system 110 may be implemented with hardware components and/or software instructions to perform one or more operations consistent with the disclosed embodiments (e.g., the example embodiments described with reference to FIGS. 1-4). The software instructions may be incorporated into a single computer or any additional or alternative computing device/system (e.g., a single server, multiple devices etc.). The system 110 may also include or associate with distributed computing devices and computing systems, and may execute software instructions on separate computing systems by remotely communicating over a network (e.g., the communications network 140). The system 110 may also implement aspects of the disclosed embodiments without accessing other devices or networks, such as communications network 140. The system 110 may also be implemented with one or more data storages for storing information consistent with the embodiments described below.

Although the systems/devices of the environment 100 are shown as being directly connected, the system 110 may be indirectly connected to one or more of the other systems/devices of the environment 100. In some embodiments, the system 110 may be only directly connected to one or more of the other systems/devices of the environment 100.

It is also to be understood that the environment 100 may omit any of the devices illustrated and/or may include additional systems and/or devices not shown. It is also to be understood that more than one device and/or system may be part of the environment 100 although one of each device and/or system is illustrated in the environment 100. It is further to be understood that each of the plurality of devices and/or systems may be different or may be the same. For example, one or more of the devices of the devices may be hosted at any of the other devices.

Figure 2:
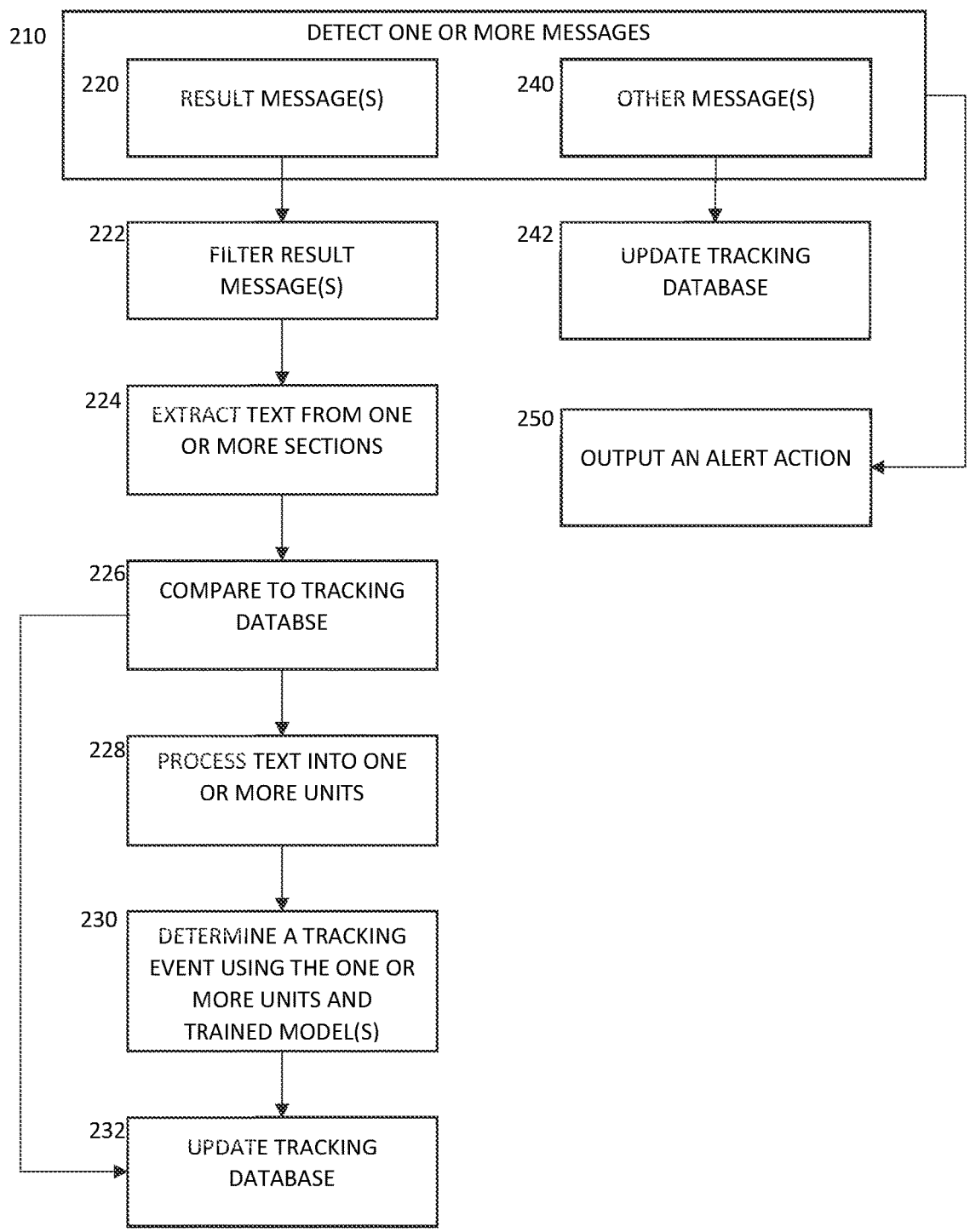
FIG. 2 shows a flowchart illustrating an example of a method of generating and monitoring one or more tracking events using the healthcare events according to embodiments.

FIG. 2 shows a flow chart 200 illustrating an example of a method of determining one or more tracking events according to certain embodiments. Operations described in flow chart 200 may be performed by a computing system, such as the system 110 described above with respect to FIG. 1 or a computing system described below with respect to FIG. 5. Although the flow chart 200 may describe the operations as a sequential process, in various embodiments, some of the operations may be performed in parallel or concurrently. In addition, the order of the operations may be rearranged. An operation may have additional steps not shown in the figure. In some embodiments, some operations may be optional. Embodiments of the method may be implemented by hardware, software, firmware, middleware, microcode, hardware description languages, or any combination thereof. When implemented in software, firmware, middleware, or microcode, the program code or code segments to perform the associated tasks may be stored in a computer-readable medium such as a storage medium.

Operations in flow chart 200 may begin at block 210, the system 110 may detect a message, an entry of information for one or more patients into an electronic medical record, that has been transmitted via an interface engine (e.g., a corepoint interface engine) using the plurality of listeners to monitor for a plurality of types of message. The processing of the message may depend on the type and/or whether it matches a (tracking) event record in the tracking database.

If the ORU listener determines that an ORU message (e.g., message marked as a "Final" and/or "Corrected") has been received (step at block 220), the system 110 may process that ORU message to determine one or more tracking events and/or to determine whether a tracking event is satisfied for a patient record (steps at blocks 222-232). If the other listeners determine that another message (e.g., ORM, ADT, SIU and/or ORU) matching a tracking event for that patient record in the tracking database was received, for example, using the patient identifier and extracted message text, the system may process that message (steps at blocks 240-242) at block 210.

In some embodiments, before block 222, the system 110 may store the information from the message into the tracking database and/or the routing database. In some embodiments, the system 110 may store the information in the routing database 110 for queuing, batching, and/or backup before each step.

In some embodiments, at block 224, the system 110 may extract text from one or more sections of the ORU message. For example, the text may be extracted from the Report Section.

In some embodiments, at block 226, the system 110 may determine whether there is a tracking event in the tracking database for that patient, for example, by comparing the extracted message text and patient identifier provided in the message to the records in the tracking database. If the system 110 determines that the patient identifier in the message matches a record in the tracking database, the system 110 may compare the extracted message text to the tracking event associated with the record. If the system 110 determines that the extracted text in that ORU message indicates that the tracking event has been satisfied, the system 110 may update the tracking database (step at block 232), for example, by removing that record.

Next, at block 228, the system 110 may process the (extracted) text into one or more units, for example, using the module 114. By way of example, the module 114 may use a plurality of tokenizers to tokenize every word in the extracted text. In some examples, an ORU message may both satisfy a tracking event and result in a generation of new tracking event(s).

Figure 3:
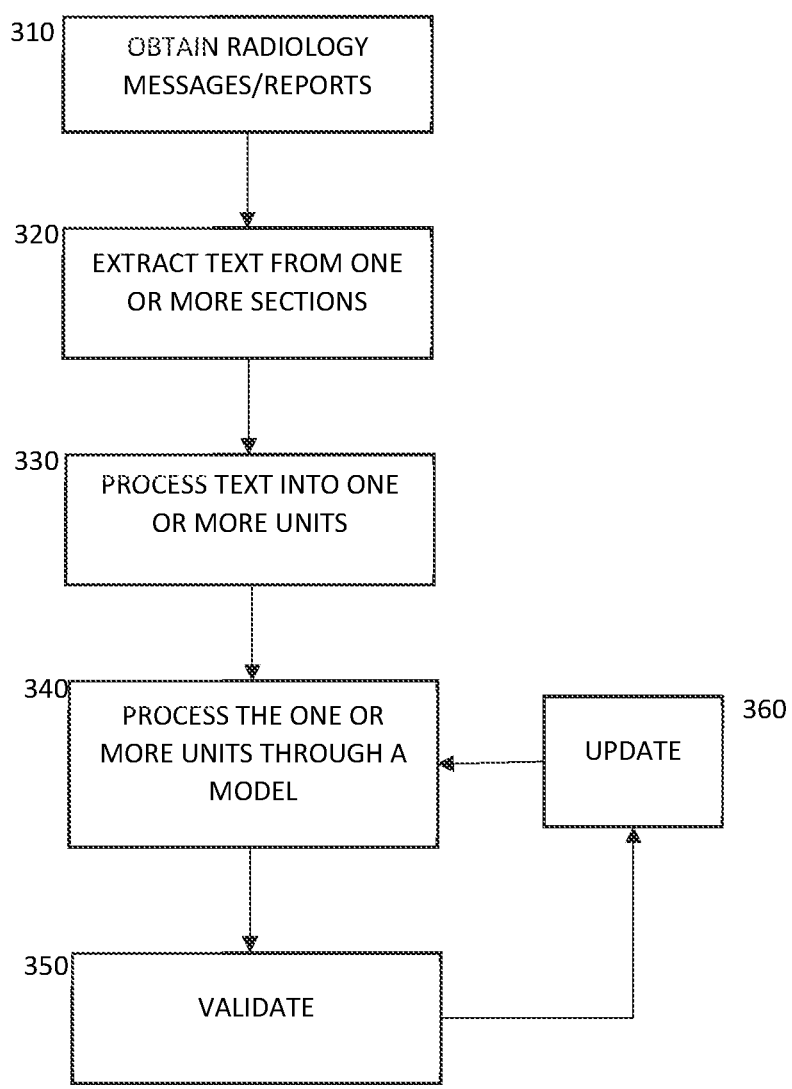
FIG. 3 shows a flowchart illustrating an example of a method of generating a trained machine learning model for determining a tracking event according to embodiments.

In some embodiments, at block 230, the system 110 may determine one or more tracking events for that message using the one or more units and the plurality of trained models. For example, each unit of text may be simultaneously processed through each trained model to determine one or more tracking events to be generated based on that message. FIG. 3 shows an example of training a model according to embodiments.

Next, at block 232, the system 110 may update the tracking database to include the one or more tracking events (information) determined at block 230 and/or to remove the one or more tracking events determined to be satisfied at block 226 for that patient. For example, if a tracking event category (such as second category) other than no follow-up (e.g., first category) is determined, the system 110 may add (i) the determined tracking event(s), for example, by adding the event code, to the corresponding record in the tracking database and/or (ii) add the determined tracking event(s), for example, by adding the event code, and the corresponding patient information to the tracking database. If no follow-up is determined, the system 110 may remove the record from the tracking database, if stored before the step at block 222. In some examples, if that tracking event is determined to be satisfied at block 226, the system 110 may remove the tracking event and/or record from the tracking database.

In some embodiments, if the listener(s) determines that one of the other (received) messages (e.g., SIU, ADT, ORM, etc.) matches a tracking event associated with that record (patient identifier) in the tracking database (at block 240) using the text of the message, the system 110 may cause the tracking database to be updated at block 242. For example, the system 110 may remove the record from the tracking database. In some embodiments, the system 110 may add that record to an analysis database.

In some embodiments, the system 110 may cause the listeners to check for messages at blocks 220 and 240 at monitoring intervals corresponding to the event code(s) to determine whether a tracking event has been completed/satisfied according to the monitoring pattern associated with the tracking event type (e.g., code). If, at block 250, the system 110 determines that messages satisfying a specific tracking event has not been received, the system 110 may cause an alert action (e.g., a clinically actionable communication) to be transmitted to the provider for that record. For example, the system 110 cause a notification to be transmitted via the healthcare information systems to the provider. In some examples, the notification may include a user interface that allows one-click ordering with EMR, allows selection of one or more reasons for failure to satisfy the tracking event by the deadline indicated by the event code, among others, or a combination thereof.

FIG. 3 shows a flow chart 300 illustrating an example of a method of generating a trained machine learning model specific to one or more tracking variables (e.g., diagnosis, procedure, type of clinic visit, etc.) using tokenized text for one or more sections and/or subsections of a message (e.g., Report section of ORU message(s)) for determining one or more tracking events (no follow-up, type of follow-up, etc.). The method may be repeated for each tracking variable and/or combination of tracking variables (findings, procedure, type of clinic visit, etc.), tracking event, among others, or any combination thereof.

In some examples, at block 310, ORU messages (e.g., (radiology) report section) for one or more imaging modalities (x-ray, CT, etc.) for a period of time may be obtained specific to the tracking event, tracking variable(s), among others, or any combination thereof.

In some embodiments, at block 320, the radiology reports may be parsed to extract text from one or more sections of the ORU message. For example, the text may be parsed from the Report Section so as to obtain the summary of findings, recommendations for clinical-follow-up, imaging, etc.

Next, at block 330, the (extracted) text may be processed into one or more units (e.g., sequences of integers), for example, using a plurality of tokenizers that can tokenize every word in the extracted text.

In some embodiments, at block 340, the one or more units may be processed through a machine learning model to train that model to generate a tracking event. By way of example, the model may be a deep learning model, such as LSTM.

Next, at block 350, the model may be validated by comparing the generated tracking events to tracking events for follow-up variable(s) provided in a validation data set (e.g., a labeled data set with ground truth). Based on that comparison, the model weights may be updated at block 360. Steps at blocks 310-360 may be repeated until the determined tracking events at block 340 meets a threshold at block 350 and/or a number of epochs. After the model has been trained, it may be saved in storage 120 for use by the tracking determination module 116.

Figure 4:
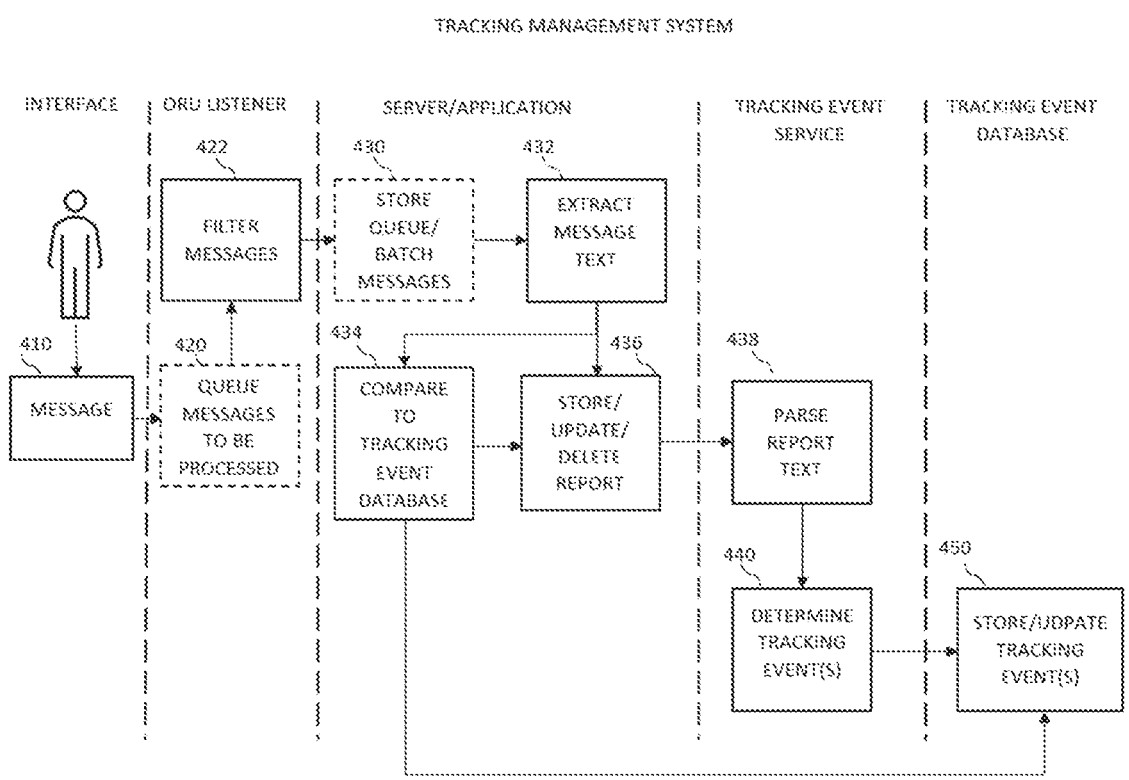
FIG. 4 shows a flow diagram of a process for generating and monitoring tracking events using an exemplary system environment according to embodiments.

FIG. 4 shows a flow diagram of a process for generating and monitoring a tracking event in an example of architecture 400 of the tracking event system 110 in accordance with some embodiments. In this example, the tracking event system 110 may include a web application server, a cloud-based application, an edge server, among others, or a combination thereof.

At block 410, a message, for example, related to results associated with a patient and placed by the provider transmitted through the hospital information systems (i.e., an ORU message) can be received by an interface of an application/server of the tracking event system according to embodiments. Next, at block 420, a listener of the system can optionally temporarily store the messages in a queue to be processed. Next, at block 422, each message can be filtered based on the status so that only messages that include final and/or corrected reports will be processed by the tracking event system. By having the queue, the process can be turned off and messages can be queued. This way, the processing to the application/server can be controlled. In this example, the architecture can use an asynchronous processing design to manage workload and allows modules to be stopped as needed.

Next, at block 430, the filtered messages (e.g., messages with marked as "Final" and/or "Corrected" reports) may be received by the ORU listener and optionally stored in queue and/or batch in a database of the application/server. Like the queuing by the ORU listener, the messages may be stored in the database using an asynchronous model. This queuing approach provide an ability to control how much processing is performed. This can control the processing to be performed by the tracking event service.

Next, at block 432, a listener of the application/server may extract the text of the message. For example, the text of the Report section of a result message may be extracted. The listener may also cause the report text to be temporarily stored at block 436.

In some examples, at block 434, the application/server may compare the patient information (e.g., patient identifier) associated with the message to the patient information (patient identifiers) associated with the records in the tracking event database to determine whether the tracking database has a record stored for that patient. If the application/server determines that there is a stored record and the report included in the message (block 432) supersedes a prior Report (e.g., report marked as "Corrected" and/or message text includes "addendum") for a patient, it can cause the prior Report to be cancelled or deleted in the application's/server's database and the one or more sections/subsections of the "new" Report to be saved to that record at block 436.

If the application/server determines that there is a stored record and the extract text satisfies the tracking event associated with that record, the application/server may compare the extracted message text with event code associated that record to determine whether the tracking event associated with that record for that patient is satisfied. For example, the application/server may compare the exam type and timestamp provided in the extract message text to the tracking event type and deadline associated with the event code to determine whether a tracking event is satisfied. If the application/server determines that the tracking event is satisfied, the application/server may cause the tracking event database to be updated, for example, by removing that record from the database at block 450.

Next, at block 438, the extracted message text may be transmitted to the tracking event service so that the extracted message text from one or more sections and/or subsections of the message may be parsed. For example, the text from Impression section, Organ-by-organ Description section, etc. may be extracted.

Next, at block 440, the parsed text may be processed so that the tracking event may be determined. In some examples, the tracking event service may include tokenizers that can process the parsed text into one or more units. The tracking event service may also use a plurality of stored models, for example, trained according to FIG. 3, to process the one or more units to generate one or more tracking events. For example, the tracking event service may cause the one or more units to be processed by each stored model simultaneously to generate one or more tracking events. By way of example, each model may be specific to a follow-up variable (e.g., diagnosis (e.g., pneumonia, pulmonary nodules, etc.), clinic visit type, procedure type, etc.) and may be trained according to the method discussed in FIG. 3. The tracking event service may determine an event code for each tracking event identified in the parsed text using the trained models.

Next, at block 450, the tracking event(s) may be transmitted to the tracking event database to be stored along with the corresponding Report information extracted at block 432 in a record in the tracking event database. For example, one or more event codes corresponding to the one or more tracking events along with the associated with message text may be transmitted to be stored in the database for that patient identifier. The rules associated with the event code may also be stored in the tracking event database.

By having a tracking event database that is based only on the generated tracking event codes, the monitoring of messages to determine whether a follow-up event is satisfied may be more accurate and efficient. Because the tracking event database has isolated only the information needed, not all information has to be processed to determine whether a tracking event is satisfied. This can allow the system to operate efficiently and accurately without overloading system.

Figure 5:
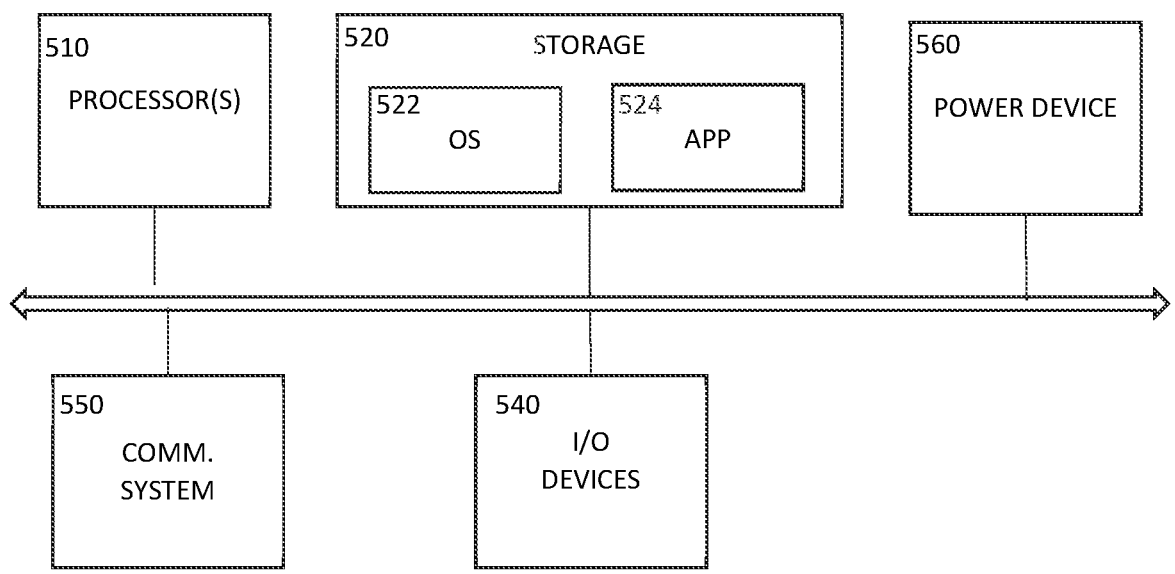
FIG. 5 is a simplified block diagram of an example of a computing system for implementing certain embodiments disclosed herein.

FIG. 5 depicts a block diagram of an example computing system 500 for implementing certain embodiments. For example, in some aspects, the computer system 500 may include computing systems associated with a device (e.g., the system 110) performing one or more processes (e.g., FIGS. 2-4) disclosed herein. The block diagram illustrates some electronic components or subsystems of the computing system. The computing system 500 depicted in FIG. 5 is merely an example and is not intended to unduly limit the scope of inventive embodiments recited in the claims. One of ordinary skill in the art would recognize many possible variations, alternatives, and modifications. For example, in some implementations, the computing system 500 may have more or fewer subsystems than those shown in FIG. 5, may combine two or more subsystems, or may have a different configuration or arrangement of subsystems.

In the example shown in FIG. 5, the computing system 500 may include one or more processing units 510 and storage 520. The processing units 510 may be configured to execute instructions for performing various operations, and can include, for example, a micro-controller, a general-purpose processor, or a microprocessor suitable for implementation within a portable electronic device, such as a Raspberry Pi. The processing units 510 may be communicatively coupled with a plurality of components within the computing system 500. For example, the processing units 510 may communicate with other components across a bus. The bus may be any subsystem adapted to transfer data within the computing system 500. The bus may include a plurality of computer buses and additional circuitry to transfer data.

In some embodiments, the processing units 510 may be coupled to the storage 520. In some embodiments, the storage 520 may offer both short-term and long-term storage and may be divided into several units. The storage 520 may be volatile, such as static random access memory (SRAM) and/or dynamic random access memory (DRAM), and/or non-volatile, such as read-only memory (ROM), flash memory, and the like. Furthermore, the storage 520 may include removable storage devices, such as secure digital (SD) cards. The storage 520 may provide storage of computer readable instructions, data structures, program modules, audio recordings, image files, video recordings, and other data for the computing system 500. In some embodiments, the storage 520 may be distributed into different hardware modules. A set of instructions and/or code might be stored on the storage 520. The instructions might take the form of executable code that may be executable by the computing system 500, and/or might take the form of source and/or installable code, which, upon compilation and/or installation on the computing system 500 (e.g., using any of a variety of generally available compilers, installation programs, compression/decompression utilities, and the like), may take the form of executable code.

In some embodiments, the storage 520 may store a plurality of application modules 524, which may include any number of applications, such as applications for controlling input/output (I/O) devices 540. The application modules 524 may include particular instructions to be executed by the processing units 510. In some embodiments, certain applications or parts of the application modules 524 may be executable by other hardware modules, such as a communication subsystem 550. In certain embodiments, the storage 520 may additionally include secure memory, which may include additional security controls to prevent copying or other unauthorized access to secure information.

In some embodiments, the storage 520 may include an operating system 522 loaded therein, such as an Android operating system or any other operating system suitable for mobile devices or portable devices. The operating system 522 may be operable to initiate the execution of the instructions provided by the application modules 524 and/or manage other hardware modules as well as interfaces with a communication subsystem 550 which may include one or more wireless or wired transceivers. The operating system 522 may be adapted to perform other operations across the components of the computing system 500 including threading, resource management, data storage control, and other similar functionality.

The communication subsystem 550 may include, for example, an infrared communication device, a wireless communication device and/or chipset (such as a Bluetooth® device, an IEEE 802.11 (Wi-Fi) device, a WiMax device, cellular communication facilities, and the like), NFC, Zig-Bee, and/or similar communication interfaces. The computing system 500 may include one or more antennas (not shown in FIG. 5) for wireless communication as part of the communication subsystem 550 or as a separate component coupled to any portion of the system.

Depending on desired functionality, the communication subsystem 550 may include separate transceivers to communicate with base transceiver stations and other wireless devices and access points, which may include communicating with different data networks and/or network types, such as wireless wide-area networks (WWANs), WLANs, or wireless personal area networks (WPANs). A WWAN may be, for example, a WiMax (IEEE 802.9) network. A WLAN may be, for example, an IEEE 802.11x network. A WPAN may be, for example, a Bluetooth network, an IEEE 802.15x, or some other types of network. The techniques described herein may also be used for any combination of WWAN, WLAN, and/or WPAN. In some embodiments, the communications subsystem 550 may include wired communication devices, such as Universal Serial Bus (USB) devices, Universal Asynchronous Receiver/Transmitter (UART) devices, Ethernet devices, and the like. The communications subsystem 550 may permit data to be exchanged with a network, other computing systems, and/or any other devices described herein. The communication subsystem 550 may include a means for transmitting or receiving data, such as identifiers of portable goal tracking devices, position data, a geographic map, a heat map, photos, or videos, using antennas and wireless links. The communication subsystem 550, the processing units 510, and the storage 520 may together comprise at least a part of one or more of a means for performing some functions disclosed herein.

The computing system 500 may include one or more I/O devices 540, such as sensors 550, a switch, a camera, a microphone or audio recorder, a communication port, or the like.

In some embodiments, the I/O devices 540 may include a microphone or audio recorder that may be used to record an audio message. The microphone and audio recorder may include, for example, a condenser or capacitive microphone using silicon diaphragms, a piezoelectric acoustic sensor, or an electret microphone. In some embodiments, the microphone and audio recorder may be a voice-activated device. In some embodiments, the microphone and audio recorder may record an audio clip in a digital format, such as MP5, WAV, WMA, DSS, etc. The recorded audio files may be saved to the storage 520 or may be sent to the one or more network servers through the communication subsystem 550.

In some embodiments, the I/O devices 540 may include a location tracking device, such as a global positioning system (GPS) receiver. In some embodiments, the I/O devices 540 may include a wired communication port, such as a micro-USB, Lightning, or Thunderbolt transceiver.

The I/O devices 540 may also include, for example, a speaker, a media player, a display device, a communication port, or the like. For example, the I/O devices 540 may include a display device, such as an LED or LCD display and the corresponding driver circuit. The I/O devices 540 may include a text, audio, or video player that may display a text message, play an audio clip, or display a video clip.

The computing system 500 may include a power device 560.

The computing system 500 may be implemented in many different ways. In some embodiments, the different components of the computing system 500 described above may be integrated to a same printed circuit board. In some embodiments, the different components of the computing system 500 described above may be placed in different physical locations and interconnected by, for example, electrical wires. The computing system 500 may be implemented in various physical forms and may have various external appearances. The components of computing system 500 may be positioned based on the specific physical form.

The methods, systems, and devices discussed above are examples. Various embodiments may omit, substitute, or add various procedures or components as appropriate. For instance, in alternative configurations, the methods described may be performed in an order different from that described, and/or various stages may be added, omitted, and/or combined. Also, features described with respect to certain embodiments may be combined in various other embodiments. Different aspects and elements of the embodiments may be combined in a similar manner. Also, technology evolves and, thus, many of the elements are examples that do not limit the scope of the disclosure to those specific examples.

The foregoing method descriptions and the process flow diagrams are provided merely as illustrative examples and are not intended to require or imply that the operations of various embodiments must be performed in the order presented. As will be appreciated by one of skill in the art the order of operations in the foregoing embodiments may be performed in any order. Words such as "thereafter," "then," "next," etc. are not intended to limit the order of the operations; these words are simply used to guide the reader through the description of the methods. Further, any reference to claim elements in the singular, for example, using the articles "a," "an" or "the" is not to be construed as limiting the element to the singular.

While the terms "first" and "second" are used herein to describe data transmission associated with a subscription and data receiving associated with a different subscription, such identifiers are merely for convenience and are not meant to limit various embodiments to a particular order, sequence, type of network or carrier.

Various illustrative logical blocks, modules, circuits, and algorithm operations described in connection with the embodiments disclosed herein may be implemented as electronic hardware, computer software, or combinations of both. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. Skilled artisans may implement the described functionality in varying ways for each particular application, but such embodiment decisions should not be interpreted as causing a departure from the scope of the claims.

The hardware used to implement various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing systems, (e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

In one or more example embodiments, the functions described may be implemented in hardware, software, firmware, or any combination thereof. If implemented in software, the functions may be stored as one or more instructions or code on a non-transitory computer readable medium or non-transitory processor-readable medium. The operations of a method or algorithm disclosed herein may be embodied in a processor-executable software module, which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

Those of skill in the art will appreciate that information and signals used to communicate the messages described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Terms, "and" and "or" as used herein, may include a variety of meanings that also is expected to depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein may be used to describe any feature, structure, or characteristic in the singular or may be used to describe some combination of features, structures, or characteristics. However, it should be noted that this is merely an illustrative example and claimed subject matter is not limited to this example. Furthermore, the term "at least one of" if used to associate a list, such as A, B, or C, can be interpreted to mean any combination of A, B, and/or C, such as A, AB, AC, BC, AA, ABC, AAB, AABBCCC, and the like.

Further, while certain embodiments have been described using a particular combination of hardware and software, it should be recognized that other combinations of hardware and software are also possible. Certain embodiments may be implemented only in hardware, or only in software, or using combinations thereof. In one example, software may be implemented with a computer program product containing computer program code or instructions executable by one or more processors for performing any or all of the steps, operations, or processes described in this disclosure, where the computer program may be stored on a non-transitory computer readable medium. The various processes described herein can be implemented on the same processor or different processors in any combination.

Where devices, systems, components or modules are described as being configured to perform certain operations or functions, such configuration can be accomplished, for example, by designing electronic circuits to perform the operation, by programming programmable electronic circuits (such as microprocessors) to perform the operation such as by executing computer instructions or code, or processors or cores programmed to execute code or instructions stored on a non-transitory memory medium, or any combination thereof. Processes can communicate using a variety of techniques, including, but not limited to, conventional techniques for inter-process communications, and different pairs of processes may use different techniques, or the same pair of processes may use different techniques at different times.

The disclosures of each and every publication cited herein are hereby incorporated herein by reference in their entirety.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A method for generating and/or monitoring a tracking event, comprising:
    providing a healthcare system environment, the healthcare system environment including a plurality of healthcare information systems and a plurality of listeners configured to detect one or more messages of a plurality of types of healthcare data messages;
    detecting, using the plurality of listeners, one or more healthcare data messages of the plurality of types of healthcare data messages associated with healthcare of a patient transmitted from one or more of the plurality of healthcare information systems, the plurality of types of healthcare data messages including a first type and one or more of other types of healthcare data messages, each listener being specific to a type of healthcare data message;
    if a first listener of the plurality of listeners determines that the one or more healthcare data messages is the first type, extracting text of each message of the first type;
    tokenizing the extracted text of each message to determine one or more units of text;
    generating one or more tracking events by applying one or more trained models to each unit of text of each message; and
    storing one or more event codes corresponding to the one or more tracking events in a record for the patient in a tracking event database, the one or more event codes being associated with a deadline for satisfaction;
    wherein the first type of healthcare data message is a message associated with results.

2. The method according to claim 1, wherein:
    the plurality of types of healthcare data messages are obtained from an interface engine that communicates with the plurality of healthcare information systems provided in the healthcare system environment.

3. The method according to claim 1, wherein the first type of healthcare data message is an ORU message.

4. The method according to claim 1, wherein when the one or more healthcare data messages is the one or more of other types of healthcare data messages and is associated with a tracking event stored in the tracking event database, the method comprising:
    processing the one or more other types of healthcare data messages according to a monitoring pattern associated with each event code stored in the tracking event database to determine whether the corresponding tracking event is satisfied.

5. The method according to claim 1, wherein the other types of healthcare data messages includes a message associated with orders, a message associated with scheduling and/or a message associated with patient administration.

6. The method according to claim 5, wherein the other types of healthcare data messages includes order entry message (ORM), admit discharge message (ADT), and/or scheduling information unsolicited (SIU) message.

7. The method according to claim 1, further comprising:
    comparing a patient identifier associated with each healthcare data message of the first type to each patient identifier associated with a record in the tracking event database;
    if the patient identifier corresponds to a record in the tracking event database, comparing the extracted text to the event code to determine whether the tracking event is satisfied; and
    if the tracking event is satisfied, updating the tracking database.

8. The method according to claim 1, further comprising:
    causing an alert notification enabling a clinical action if a healthcare data message does not satisfy the deadline associated with each tracking event record.

9. The method according to claim 8, wherein the alert notification includes a user interface configured to order a procedure and/or a user interface configured to select one or more reasons for failure to satisfy the tracking event by the deadline indicated by the event code.

10. The method according to claim 1, further comprising:
    filtering messages each healthcare data messages, using the respective listener, based on a status of report included in each message; and
    wherein each listener only processes messages that has the status of final and/or corrected.

11. A system for generating and/or monitoring a tracking event, comprising:
    a plurality of healthcare information systems; and
    a tracking management system, the tracking management system including:
        a plurality of listeners configured to detect one or more messages of a plurality of types of healthcare data messages;
        a memory; and
        one or more processors, wherein the one or more processors is configured to cause:
            detecting, using the plurality of listeners, one or more healthcare data messages of the plurality of types of healthcare data messages associated with healthcare of a patient transmitted from one or more of the plurality of healthcare information systems, the plurality of types of healthcare data messages including a first type and one or more of other types of healthcare data messages, each listener being specific to a type of healthcare data message;

if a first listener of the plurality of listeners determines that the one or more healthcare data messages is the first type, extracting text of each message of the first type;

tokenizing the extracted text of each message to determine one or more units of text;

generating one or more tracking events by applying one or more trained models to each unit of text of each message; and storing one or more event codes corresponding to the one or more tracking events in a record for the patient in a tracking event database, the one or more event codes being associated with a deadline for satisfaction wherein the first type of healthcare data message is a message associated with results.

12. The system according to claim 11, wherein:

the plurality of types of healthcare data messages are obtained from an interface engine that communicates with the plurality of healthcare information systems provided in the healthcare system environment.

13. The system according to claim 1, wherein the first type of healthcare data message is an ORU message.

14. The system according to claim 11, wherein:

when the one or more healthcare data messages is the one or more of other types of healthcare data messages and is associated with a tracking event stored in the tracking event database;

the processor is further configured to cause:

processing the one or more other types of healthcare data messages according to a monitoring pattern associated with each event code stored in the tracking event database to determine whether the corresponding tracking event is satisfied.

15. The system according to claim 11, wherein the other types of healthcare data messages includes a message associated with orders, a message associated with scheduling and/or a message associated with patient administration.

16. The system according to claim 15, wherein the other types of healthcare data messages includes order entry message (ORM), admit discharge message (ADT), and/or scheduling information unsolicited (SIU) message.

17. The system according to claim 11, wherein the processor is further configured to cause:

comparing a patient identifier associated with each healthcare data message of the first type to each patient identifier associated with a record in the tracking event database;

if the patient identifier corresponds to a record in the tracking event database, comparing the extracted text to the event code to determine whether the tracking event is satisfied; and if the tracking event is satisfied, updating the tracking database.

18. The system according to claim 11, wherein the processor is further configured to cause:

causing an alert notification enabling a clinical action if a healthcare data message does not satisfy the deadline associated with each tracking event record.

19. The system according to claim 18, wherein the alert notification includes a user interface configured to order a procedure and/or a user interface configured to select one or more reasons for failure to satisfy the tracking event by the deadline indicated by the event code.

20. The system according to claim 11, wherein the processor is further configured to cause:

filtering messages each healthcare data messages, using the respective listener, based on a status of report included in each message; and wherein each listener only processes messages that has the status of final and/or corrected.

* * * * *